US012246078B2

(12) United States Patent
Curatola

(10) Patent No.: US 12,246,078 B2
(45) Date of Patent: Mar. 11, 2025

(54) ORAL CARE FORMULATIONS AND METHODS FOR USE

(71) Applicant: Gerald P. Curatola, New York, NY (US)

(72) Inventor: Gerald P. Curatola, New York, NY (US)

( * ) Notice: Subject to any disclaimer, the term of this patent is extended or adjusted under 35 U.S.C. 154(b) by 355 days.

(21) Appl. No.: 16/123,415

(22) Filed: Sep. 6, 2018

(65) Prior Publication Data

US 2019/0076343 A1 Mar. 14, 2019

Related U.S. Application Data

(60) Provisional application No. 62/558,571, filed on Sep. 14, 2017.

(51) Int. Cl.

| *A61K 8/35* | (2006.01) |
| *A61K 8/23* | (2006.01) |
| *A61K 8/34* | (2006.01) |
| *A61K 8/67* | (2006.01) |
| *A61K 8/97* | (2017.01) |
| *A61K 8/9789* | (2017.01) |
| *A61K 8/98* | (2006.01) |
| *A61Q 11/00* | (2006.01) |

(52) U.S. Cl.
CPC ............... *A61K 8/35* (2013.01); *A61K 8/23* (2013.01); *A61K 8/347* (2013.01); *A61K 8/355* (2013.01); *A61K 8/67* (2013.01); *A61K 8/671* (2013.01); *A61K 8/673* (2013.01); *A61K 8/676* (2013.01); *A61K 8/678* (2013.01); *A61K 8/97* (2013.01); *A61K 8/9789* (2017.08); *A61K 8/988* (2013.01); *A61Q 11/00* (2013.01); *A61K 2800/5922* (2013.01)

(58) Field of Classification Search
CPC . A61K 8/676; A61K 8/23; A61K 8/97; A61K 8/35; A61K 8/347; A61K 8/67; A61K 8/678; A61K 8/671; A61K 8/988; A61K 8/673; A61K 8/9789; A61K 8/355; A61K 2800/5922; A61Q 11/00
See application file for complete search history.

(56) References Cited

U.S. PATENT DOCUMENTS

| 3,992,519 | A | | 11/1976 | Hofmann | |
| 4,440,745 | A | * | 4/1984 | Schmidt | C09K 3/1454 |
| | | | | | 424/78.03 |
| 6,503,483 | B2 | | 1/2003 | Shuch | |
| 8,506,953 | B2 | | 8/2013 | Bottner | |
| 8,563,053 | B2 | * | 10/2013 | Mousa | A61K 36/31 |
| | | | | | 424/755 |
| 8,728,446 | B2 | | 5/2014 | Hurwitz | |
| 9,554,986 | B2 | | 1/2017 | Harvey | |
| 9,987,217 | B2 | * | 6/2018 | Herrmann | A61P 43/00 |
| 10,172,786 | B2 | | 1/2019 | Anastassov et al. | |
| 2004/0067204 | A1 | * | 4/2004 | Wolf | A61K 8/673 |
| | | | | | 424/49 |
| 2004/0258634 | A1 | | 12/2004 | Cazor et al. | |
| 2006/0142184 | A1 | | 6/2006 | Bannister | |
| 2009/0238774 | A1 | | 9/2009 | Connolly | |
| 2012/0237456 | A1 | * | 9/2012 | Trivedi | A61P 1/02 |
| | | | | | 424/48 |

FOREIGN PATENT DOCUMENTS

| CA | 1237081 A | | 5/1988 |
| CN | 104288082 A | * | 1/2015 |
| CN | 105434263 A | | 3/2016 |
| EP | 0117321 | | 9/1984 |
| EP | 2815654 | | 12/2014 |
| EP | 2815654 A1 | | 12/2014 |
| JP | S63179823 A | | 7/1988 |
| WO | 2006060145 A2 | | 6/2006 |
| WO | WO 2012068730 | * | 11/2010 |
| WO | 2014191009 A1 | | 12/2014 |
| WO | 2015017625 A1 | | 2/2015 |
| WO | WO2015017625 | | 2/2015 |
| WO | 2015099755 A1 | | 7/2015 |
| WO | WO 2016100516 | * | 6/2016 |

OTHER PUBLICATIONS

Gordeladze et al., Vitamin K2: Vital for Health and Wellbeing, "Vitamin K2 and its impact on tooth epigenetics", p. 27, Mar. 2017.*
Geleijnse JM, Vermeer C, Grobbee DE, et al. Dietary intake of menaquinone is associated with a reduced risk of coronary heart disease: the Rotterdam Study. J Nutr. Nov. 2004;134(11):3100-5.
Bostrom K, Watson KE, Horn S, et al. Bone morphogenetic protein expression in human atherosclerotic lesions. J Clin Invest. Apr. 1993;91(4):1800-9.
Abedin M, Tintut Y, Demer LL. Vascular calcification: mechanisms and clinical ramifications. Arterioscler Thromb Vasc Biol. Jul. 2004;24(7):1161-70.
Schurgers LJ, Dissel PE, Spronk HM, et al. Role of vitamin K and vitamin K-dependent proteins in vascular calcification. Z Kardiol. 2001;90 Suppl 3:57-63, Abstract Only.
Iwamoto J, Takeda T, Sato Y. Menatetrenone (vitamin K2) and bone quality in the treatment of postmenopausal osteoporosis. Nutr Rev. Dec. 2006;64(12):509-17.
Kaneki M, Hodges SJ, Hosoi T, et al. Japanese fermented soybean food as the major determinant of the large geographic difference in circulating levels of vitamin K2: possible implications for hip-fracture risk. Nutrition. Apr. 2001;17(4):315-21.

(Continued)

*Primary Examiner* — Lezah Roberts
(74) *Attorney, Agent, or Firm* — Lerner David LLP

(57) ABSTRACT

An oral care product comprising at least one of phytomenadione (vitamin $K_1$), menaquinone (vitamin $K_2$), vitamin C, selenium, ubiquinone (Coenzyme $Q_{10}$), *Astragalus*, Ginseng, *Schisandra*, adaptogenic herbs, cannabidiol, or the like. An oral care product directed toward rebalancing micro-bacterial homeostasis in the mouth, or establishing and maintaining a healthy oral microbiome.

10 Claims, No Drawings

(56) References Cited

OTHER PUBLICATIONS

Shiraki M, Shiraki Y, Aoki C, Miura M. Vitamin K2 (menatetrenone) effectively prevents fractures and sustains lumbar bone mineral density in osteoporosis. J Bone Miner Res. Mar. 2000;15(3):515-21.
Iwamoto J, Takeda T, Ichimura S. Combined treatment with vitamin K2 and bisphosphonate in postmenopausal women with osteoporosis. Yonsei Med J. Oct. 30, 2003;44(5):751-6.
Iwamoto J, Takeda T, Sato Y. Effects of vitamin K2 on osteoporosis. Curr Pharm Des. 2004;10(21):2557-76.
Schurgers LJ, Teunissen KJ, Knapen MH, et al. Novel conformation-specific antibodies against matrix gamma-carboxyglutamic acid (Gla) protein: undercarboxylated matrix Gla protein as marker for vascular calcification. Arterioscler Thromb Vasc Biol. Aug. 2005;25(8):1629-33.
Luo G, Ducy P, McKee MD, et al. Spontaneous calcification of arteries and cartilage in mice lacking matrix GLA protein. Nature. Mar. 6, 1997;386(6620):78-81.
Wang Y, Zhang W, Zhang Y, et al. VKORC1 haplotypes are associated with arterial vascular diseases (stroke, coronary heart disease, and aortic dissection). Circulation. Mar. 28, 2006;113(12):1615-21.
Gage BF, Birman-Deych E, Radford MJ, Nilasena DS, Binder EF. Risk of osteoporotic fracture in elderly patients taking warfarin: results from the National Registry of Atrial Fibrillation 2. Arch Intern Med. Jan. 23, 2006;166(2):241-6.
Schurgers LJ, Aebert H, Vermeer C, Bultmann B, Janzen J. Oral anticoagulant treatment: friend or foe in cardiovascular disease? Blood. Nov. 15, 2004;104(10):3231-2.
Habu D, Shiomi S, Tamori A, et al. Role of vitamin K2 in the development of hepatocellular carcinoma in women with viral cirrhosis of the liver. JAMA. Jul. 21, 2004;292(3):358-61.
Mizuta T, Ozaki I, Eguchi Y, et al. The effect of menatetrenone, a vitamin K2 analog, on disease recurrence and survival in patients with hepatocellular carcinoma after curative treatment: a pilot study. Cancer. Feb. 15, 2006;106(4):867-72.
Tsujioka T, Miura Y, Otsuki T, et al. The mechanisms of vitamin K2-induced apoptosis of myeloma cells. Haematologica. May 2006;91(5):613-9.
Hojo K, Watanabe R, Mori T, Taketomo N. Quantitative measurement of tetrahydromenaquinone-9 in cheese fermented by propionibacteria. J Dairy Sci. Sep. 2007;90(9):4078-83.
Shoji S. Vitamin K and vascular calcification. Clin Calcium. Aug. 2002;12(8):1123-8.
Katsuyama H, Ideguchi S, Fukunaga M, et al. Promotion of bone formation by fermented soybean (natto) intake in premenopausal women. J Nutr Sci Vitaminol (Tokyo). Apr. 2004;50(2):114-20, Abstract Only.
Sconce E, Avery P, Wynne H, Kamali F. Vitamin K supplementation can improve stability of anticoagulation for patients with unexplained variability in response to warfarin. Blood. Mar. 15, 2007;109(6):2419-23.
Database GNPD [Online] Mintel; Oct. 2012 (Oct. 2012), Calcium Bone Formula Dietary Supplement, XP002786551.
Database GNPD [Online] Mintel; Dec. 2015 (Dec. 2015), "Vitamin D Complex", XP002786552.
Database GNPD [Online] Mintel; Jun. 2017 (Jun. 2017), "Calcium, Magnesium, and Vitamins D3 and K2 Supplement", XP002786553.
Database GNPD [Online] Mintel; May 2017 (May 2017), "Vitamin K and D+ Calcium Based Food Supplement Gummies", XP002786554.
Database GNPD [Online] Mintel; Jun. 2016 (Jun. 2016), "Dietary Supplement with Calcium, Magnesium and Vitamin K2", XP002786555.
Database GNPD [Online] Mintel; May 2016 (May 2016), "Super K with Advanced K2 Complex", XP002786556.
International Search Report for Application No. PCT/US2018/050485 mailed Nov. 30, 2018. 4 pgs.

* cited by examiner

ORAL CARE FORMULATIONS AND METHODS FOR USE

RELATED APPLICATIONS

This utility patent application claims the benefit of U.S. Provisional Patent Application Ser. No. 62/558,571, filed on Sep. 14, 2017, which is hereby incorporated by reference in its entirety.

BACKGROUND

1. The Field of the Invention

This invention relates to oral care products containing a variety of components, including without limitation, probiotics, prebiotics, vitamins, minerals, herbs, and other components for promoting a healthy mouth.

2. Background

U.S. Pat. Nos. 6,503,483 and 6,207,137 and 5,925,335 are hereby incorporated by this reference in their entireties.

A wide variety of oral care products are currently available. The majority of these products are designed to clean the mouth, teeth and gums using abrasives and detergents. The primary goal of most oral care products is to kill bacteria in the mouth, or sterilize the mouth.

The mouth may be considered as having its own bacterial environment, which may be described as an oral microbiome. The oral microbiome of a mouth may include bacteria that would be considered unhealthy for the individual person for a variety of reasons. The oral microbiome of a healthy mouth can also include bacteria that would be considered healthy for the individual person. Thus, killing all the bacteria in the mouth may not be considered entirely beneficial as it would kill bacteria that are useful and necessary for maintaining a healthy mouth.

Accordingly, it would be an advance in the art of oral care products to provide an oral care product formulated to promote healthy teeth and gums and to provide treatment for chronic diseases of the mouth, while also promoting a healthy oral microbiome. Similarly, it would also be an advance in the art of oral care to provide an oral care method that helps to treat chronic diseases of the mouth and to help clean the mouth, while maintaining a healthy oral microbiome.

BRIEF SUMMARY OF THE INVENTION

In accordance with the foregoing, certain embodiments of an oral care product and methods for production and use in accordance with the invention may provide oral care products that can be used for a variety of purposes, including without limitation, improved gum tissue health, strengthening of teeth, providing pre-biotics and pro-biotics, rebalancing micro-bacterial homeostasis in the mouth, and better breath.

In one embodiment, an oral care product may be comprised of a base and an active component. An active component, or operative constituent, may include one or more compounds for enhancing and/or maintaining a healthy mouth.

An oral care product may include numerous additional substances or compounds, including without limitation, vitamins, minerals, prebiotics, prebiotic fibers, probiotics, adaptogenic herbs, or the like.

An oral care product may be provided in any number of desirable forms, including without limitation, a toothpaste, a mouthwash, a chewing gum, a lozenge, a coated interdental device, a coated dental floss, or the like.

An oral care product may comprise a base constituent and an operative constituent, wherein the operative constituent comprises an effective amount of a vitamin $K_2$ complex and an effective amount of vitamin D and an effective amount of calcium. The operative constituent may further comprise an effective amount of biotin, an effective amount of cannabidiol, an effective amount of selenium, an effective amount of vitamin A, an effective amount of vitamin E, an effective amount of vitamin C, an effective amount of ubiquinone, an effective amount of propolis, and/or an effective amount of one or more adaptogenic herbs.

An oral care product may be utilized in a variety of ways, or by a variety of methods, to promote and maintain a healthy oral microbiome. For example, a suitable toothbrush may be provided. A suitable toothpaste may be selected and an appropriate amount of the selected toothpaste placed on the toothbrush. A user may then brush their teeth in the usual manner. This brushing may produce a mouth slurry, which mouth slurry can be swished around the user's mouth before the mouth slurry is spit from the user's mouth.

DETAILED DESCRIPTION OF THE PREFERRED EMBODIMENTS

It will be readily understood that the components of the present invention, as generally described herein, could be arranged and designed in a wide variety of different configurations or formulations. Thus, the following more detailed description of the embodiments of the system, products and methods of use of the present invention, are not intended to limit the scope of the invention, as claimed, but is merely representative of various embodiments of the invention.

In one embodiment, an oral care product may include a base and an active component. A base, or base constituent, may be comprised of any suitable materials. For example, and not by way of limitation, a base may include appropriate amounts of calcium carbonate, silica, glycerine, and deionized water.

An active component, or an operative constituent, may be comprised of any suitable materials. Generally, an operative constituent may provide additional benefits to help improve and/or maintain oral health above and beyond the basic benefits provided by a base. Any number of compounds or materials may be utilized to comprise an operative constituent of an oral care product.

Suitable compounds or materials in an active component, or operative constituent, may include, without limitation, one or more of phytomenadione (vitamin $K_1$), menaquinone (vitamin $K_2$), vitamin C, selenium, ubiquinone (Coenzyme $Q_{10}$), *Astragalus*, Ginseng, *Schisandra*, various adaptogenic herbs, cannabidiol, lignite, or the like.

An oral care product, or an operative constituent, may include a component that supports another component, even if it is not directly related to oral health.

In one embodiment, vitamin K may be included in an active component, or operative constituent. Vitamin K provides numerous health benefits. For example, vitamin K helps maintain bone density by facilitating calcium transport into bone and promotes a healthy heart and vascular system. Vitamin K may be provided in various forms, for example, as vitamin $K_1$ and/or dual forms of vitamin $K_2$, menaquinone-7 (MK-7) and menaquinone-4 (MK-4).

Vitamins $K_1$ and $K_2$ both contribute to blood clotting. Vitamin $K_2$ may positively impact inflammation. Vitamin $K_2$ also works synergistically with a number of other nutrients, including at least calcium and vitamin D. Vitamin $K_2$'s biological role is to help move calcium into the proper areas in your body, such as bones and teeth. Vitamin $K_2$ activates a protein hormone called osteocalcin, produced by osteoblasts, which is needed to bind calcium into the matrix of bone. Osteocalcin also appears to help prevent calcium from depositing into arteries.

Obtaining enough vitamin K, including vitamin $K_2$, can be difficult through a normal diet. Supplementing vitamin K can be important, especially in view of its benefits associated with oral health. For example, an oral health product, and/or an operative constituent, may include an advanced vitamin $K_2$ complex that includes both forms of vitamin $K_2$, MK-4 and MK-7 (or simply, vitamin $K_2$ complex). MK-4 is most rapidly absorbed, but may only last for a few hours in the bloodstream. MK-7 may be made available to the body for at least twenty-four (24) hours and at much higher levels than MK-4.

Moreover, in another embodiment, an oral care product, and/or an operative constituent, may include calcium with an advanced vitamin $K_2$ complex. The combination of an advanced vitamin $K_2$ complex and calcium as part of an operative constituent may provide additional, synergistic benefits to a user in improving and maintaining oral health.

Moreover, in another embodiment, an oral care product, and/or an operative constituent, may include vitamin D with an advanced vitamin $K_2$ complex. Vitamin D may be described as a gatekeeper that controls what gets in, while vitamin K may be described as a traffic cop that directs where things need to go. The combination of an advanced vitamin $K_2$ complex and vitamin D as part of an operative constituent may provide additional, synergistic benefits to a user in improving and maintaining oral health.

In one embodiment, biotin (vitamin B-7) may be included in an active component, or operative constituent. Biotin is a water-soluble vitamin that is essential for healthy teeth, gum tissue, muscle function, heart, skin, hair and nails, but is generally lacking in most people. Biotin can be absorbed by the gums and mucous membranes in the mouth.

In one embodiment, cannabidiol may be included in an active component, or operative constituent. Cannabidiol is a component of marijuana, but it does not produce the psychoactive effects that have made marijuana attractive for recreational use. Cannabidiol has an anti-inflammatory effect that reduces swelling and periodontal inflammation. Cannabidiol binds to CB1 receptors in the body to relieve pain. Cannabidiol may also be effective in reducing and/or preventing oral cancer. Cannabidiol may have anti-tumor effects, for example, cannabidiol may induce tumor cell death, inhibit cancer cell growth, and thereby control and inhibit the spread of cancer cells.

In one embodiment, an active component, or an operative constituent, may include one or more adaptogenic herbs. Generally, adaptogenic herbs may be described as natural substances that work with a person's body to help them adapt to certain things, for example, to help deal productively with stress. One way adaptogenic herbs may work is by helping to regulate the hormones in a person's body. Various adaptogenic herbs may be considered and included in an oral care product.

For example, *Astragalus* root (*Astragalus membranaceus*) is an adaptogenic herb that may provide immunity-enhancing effects, complement chemotherapy treatment, provide cardiovascular protection, and promote periodontal health.

As another example, jiaogulan (*Gynostemma pentaphyllum*) is an adaptogenic herb that may improve immune function, provide detoxification, promote normal cholesterol, normalize blood pressure, help build stamina and endurance, and promote periodontal health.

As another example, acai (*Euterpe oleracea*) is an adaptogenic herb that may include anti-aging compounds, encourage normal weight regulation, prevent cardiovascular disease, and promote skin and periodontal tissue health.

As another example, Reishi mushroom or Lingzhi mushroom (*Ganoderma lucidum, Ganoderma lingzhi*) is an adaptogenic herb that may include antioxidants, benefit those with asthma, provide anti-inflammatory benefits, normalize cholesterol levels, and promote periodontal health.

As another example, ashwagandha (*Withania somnifera*) is an adaptogenic herb that may improve physical energy and endurance, boost immunity and libido, and normalize blood sugar.

As another example, horny goat weed (*Epimedium grandiflorum*) is an adaptogenic herb that may increase parasympathetic nervous activity, mitigate osteoporosis, improve libido, enhance smooth muscle tissue function, and prevent periodontal bone loss.

As another example, *Tribulus* (*Tribulus terrestris*, or Bindii) is an adaptogenic herb that may enhance athletic performance, improve circulation, improve sexual performance, improve circulation, and improve periodontal health.

As another example, *Ocimum tenuiflorum* (*Ocimum sanctum*, or holy basil) is an adaptogenic herb that may benefit cortisol levels and reduce anxiety, and improve periodontal health.

As another example, *Shisandra* (i.e., *Shisandra chinensis*) is an adaptogenic herb that may help to improve and maintain periodontal health.

As another example, ginseng in various forms (i.e., Asian Ginseng and Ginseng Eleuthero) are adaptogenic herbs that may improve mental clarity, boost natural energy, support heart health, and support immune functions.

As another example, gotu kola (*Centella asiatica*) is an adaptogenic herb that may help improve blood circulation, reduce swelling, and provide antioxidants.

In one embodiment, an active component, or an operative constituent, may include lignite. Lignite may promote a healthy gut and promote a healthy immune system. Lignite may also provide additional abrasive benefits to an oral care product.

In one embodiment, an active component, or an operative constituent, may include one or more prebiotics and/or probiotics. For example, natto, a fermented Japanese soybean, may be described as a prebiotic and is an excellent source of vitamin $K_2$, rich in MK-7.

In one embodiment, an active component, or an operative constituent, may include ubiquinone (Coenzyme $Q_{10}$). Ubiquinone is known to help enhance periodontal health.

In one embodiment, an active component, or an operative constituent, may include selenium and various vitamins, such as vitamin A, vitamin C, vitamin D and vitamin E. If vitamin A is included, it is preferably added in the form of water dispersed vitamin A acetate, a dry fish oil free form, which is included for its value in the promotion of gum tissue healing. If vitamin C is included, it is preferably added in the form of sodium ascorbate and/or calcium ascorbate, which is included for its value in the promotion of healing of the mouth from gum disease and to reduce plaque build-up on the teeth. If vitamin D is included, it is preferably in the form of vitamin D-3, which is included for its value in the reduction of inflammation and the improvement of bone density and its complimentary functionality with vitamin K. If vitamin E is included, it is preferably in the form of d-alpha tocopherol, which is included for its value in the promotion of healing of gum tissues.

In one embodiment, an active component, or an operative constituent, may include propolis, or bee glue. Propolis is a plant-based substance used by bees in the construction of germ-free hives. Propolis may be included for its use as a salve on abraded, bruised or inflamed mucous membranes.

In one embodiment, an active component, or an operative constituent, may include and appropriate amount of one or more of the following: stevia extract, *Echinacea*, grape seed extracts, cranberry extract, tangerine oil, lemon oil, methyl sulfonyl methane, pycnogenol, refined or unrefined cocoa, and homeopathic tissue salts.

Following are examples of preferred toothpaste formulations in weight percentage.

Example 1

| | |
|---|---|
| Calcium Carbonate | 32% |
| Silica | 26% |
| Glycerine | 23% |
| Deionized water | 9% |
| Vitamin $K_2$ | 2% |
| Vitamin D | 2% |
| Vitamin A | 1.9% |
| Vitamin C | 1.9% |
| Vitamin E | 1.9% |
| Tangerine oil | 0.17% |
| Lemon oil | 0.13% |

Example 2

| | |
|---|---|
| Calcium Carbonate | 32% |
| Silica | 26% |
| Glycerine | 23% |
| Deionized water | 9% |
| Vitamin $K_2$ | 2% |
| Vitamin D | 2% |
| Vitamin B-7 | 2% |
| Vitamin A | 1.8% |
| Vitamin E | 1.9% |
| Tangerine oil | 0.17% |
| Lemon oil | 0.13% |

Example 3

| | |
|---|---|
| Calcium Carbonate | 32% |
| Silica | 26% |
| Glycerine | 23% |
| Deionized water | 9% |
| Vitamin $K_2$ | 2% |
| Vitamin D | 2% |
| Vitamin A | 1.5% |
| Vitamin C | 1.5% |
| Vitamin E | 1.5% |
| Cannabidiol | 1.2% |
| Tangerine oil | 0.17% |
| Lemon oil | 0.13% |

Example 4

| | |
|---|---|
| Calcium Carbonate | 32% |
| Silica | 26% |
| Glycerine | 23% |
| Deionized water | 9% |
| Vitamin $K_2$ | 2% |
| Vitamin D | 2% |
| Vitamin B-7 | 2% |
| Vitamin C | 1% |
| Vitamin E | 1% |
| Cannabidiol | 1.2% |
| Propolis | 0.5% |
| Tangerine oil | 0.17% |
| Lemon oil | 0.13% |

Example 5

| | |
|---|---|
| Calcium Carbonate | 32% |
| Silica | 26% |
| Glycerine | 23% |
| Deionized water | 9% |
| Vitamin $K_2$ | 2% |
| Vitamin D | 2% |
| Vitamin B-7 | 2% |
| Co-enzyme Q-19 | 2% |
| Cannabidiol | 1% |
| Stevia extract | 0.7% |
| Tangerine oil | 0.17% |
| Lemon oil | 0.13% |

Following are examples of preferred prophylaxis paste formulations in weight percentage.

Example 6

| | |
|---|---|
| Calcium Carbonate | 29% |
| Silica | 25% |
| Glycerine | 9% |
| Deionized water | 9% |
| Vitamin $K_2$ | 5% |
| Vitamin D | 5% |
| Vitamin B-7 | 5% |
| Vitamin A | 4% |
| Vitamin C | 4% |
| Vitamin E | 4% |
| Stevia extract | 0.7% |
| Tangerine oil | 0.17% |
| Lemon oil | 0.13% |

Example 7

| | |
|---|---|
| Calcium Carbonate | 29% |
| Silica | 25% |
| Glycerine | 9% |
| Deionized water | 9% |
| Vitamin $K_2$ | 5% |
| Vitamin D | 5% |
| Vitamin B-7 | 5% |
| Co-enzyme Q10 | 5% |
| Propolis | 4% |
| Cannabidiol | 3% |

-continued

| | |
|---|---|
| Stevia extract | 0.7% |
| Tangerine oil | 0.17% |
| Lemon oil | 0.13% |

In one embodiment, the planned amounts of powdered, or dry ingredients (i.e., vitamins, propolis and co-enzyme Q10) are combined and milled together to produce a uniformly textured fine powder. Separately, the planned amounts of liquid ingredients (i.e., water, glycerine, Stevia extract, tangerine oil and lemon oil) are combined and thoroughly mixed. Essential oils such as tangerine and lemon oil may be used as solubilizers for the non-water soluble components of the active ingredient blend.

The dry ingredients of the formulation are then slowly added to the liquid ingredients while mixing until a homogeneous slurry is produced. To this slurry, the planned amounts of milled calcium carbonate and silica powder is added incrementally while stirring until all of this powder has been incorporated, resulting in a homogeneous mass of a suitable, paste-like composition for use as a toothpaste, a prophylaxis paste, or the like.

In one embodiment, a method of using an oral care product may be utilized. For example, and not by way of limitation, a method of using a toothpaste may be utilized.

A toothbrush may be provided for applying a toothpaste to a user's teeth, or for brushing a user's teeth. A toothbrush, or any suitable, similar instrument, may be utilized in an appropriate manner. A toothbrush may be described as having a handle and a set of bristles.

A toothpaste may be provided and/or selected for use by a user to promote and/or maintain good oral health, or to promote or maintain a healthy oral microbiome. Any suitable toothpaste formulation may be utilized. A toothpaste formulation may be selected for a specific purpose. For example, one purpose for a toothpaste having a given formulation may be to simply promote and maintain a healthy oral microbiome. Another purpose for a toothpaste having a separate formulation may be to assist in the healing of oral mucosa and oral tissues. Another purpose for a toothpaste having another separate formulation may be to prevent or treat oral tumors. The step of providing and/or selecting a toothpaste may include a number of decisions based on a desired effect and available toothpaste formulations.

A selected toothpaste, or a portion of a selected toothpaste, may be placed on the bristles of a toothbrush.

A user may use the toothbrush to brush the user's teeth. A user may be described as producing a mouth slurry while brushing the user's teeth. A mouth slurry may be comprised of fluids that are naturally present in a user's mouth, the selected toothpaste, and/or additional water added to the user's mouth via any suitable means.

A user may swish or swirl or agitate the mouth slurry around the user's mouth. This swishing of the mouth slurry may help facilitate the benefits associated with the selected toothpaste for all of the oral tissues and surfaces in the user's mouth.

A user may spit the mouth slurry from the user's mouth. A user may also use any suitable liquid to rinse the user's mouth after the mouth slurry has been spit from the user's mouth.

The subject invention may be more easily comprehended by reference to the specific embodiments recited herein, which are representative of the invention. However, it must be understood that the specific embodiments are provided only for the purpose of illustration, and that the invention may be practiced in a manner separate from what is specifically illustrated without departing from its scope and spirit.

What is claimed and desired to be secured by United States Letters Patent is:

1. A method for using a toothpaste to promote a healthy oral microbiome, the method comprising:
   providing a toothbrush for a user, wherein the toothbrush comprises a handle and a set of bristles opposite the handle;
   selecting a toothpaste consisting of a base constituent and an operative constituent;
   placing a portion of the toothpaste on the set of bristles of the toothbrush;
   brushing the teeth of a user; and
   producing a mouth slurry in the mouth of the user by the brushing,
   wherein the operative constituent consists of an effective amount of menaquinone-7, an effective amount of ubiquinone, and an effective amount of vitamin D, and, optionally, one or more selected from the group consisting of cannabidiol, vitamin A, selenium, vitamin E, propolis, lignite, biotin, prebiotic fibers, menaquinone-4, cranberry extract, stevia extract, Echinacea, grape seed extracts, cranberry extract, tangerine oil, lemon oil, methyl sulfonyl methane, pycnogenol, refined or unrefined cocoa, homeopathic tissue salts, *Astragalus, Gynostemma,* acai, *Ganoderma, Withania, Epimedium, Tribulus, Shisandra,* ginseng, *Centella,* and *Ocimum tenuiflorum,* and
   wherein the base constituent consists of one or more selected from the group consisting of calcium carbonate, silica, glycerine, and water.

2. The method of claim 1, wherein the operative constituent consists of the effective amount of menaquinone-7, the effective amount of ubiquinone, the effective amount of vitamin D, and an effective amount of the cannabidiol.

3. The method of claim 1, wherein the operative constituent consists of the effective amount of menaquinone-7, the effective amount of ubiquinone, the effective amount of vitamin D, an effective amount of the vitamin A, an effective amount of the selenium, and an effective amount of the vitamin E.

4. The method of claim 1, wherein the operative constituent consists of the effective amount of menaquinone-7, the effective amount of ubiquinone, the effective amount of vitamin D, an effective amount of the propolis, an effective amount of the lignite, an effective amount of the biotin, and an effective amount of the prebiotic fibers.

5. The method of claim 1, wherein the operative constituent consists of the effective amount of menaquinone-7, the effective amount of ubiquinone, the effective amount of vitamin D, and at least one selected from the group consisting of: the *Astragalus,* the *Gynostemma,* the acai, the *Ganoderma,* the *Withania,* the *Epimedium,* the *Tribulus,* the *Shisandra,* the ginseng, the *Centella,* and the *Ocimum tenuiflorum.*

6. The method of claim 1, wherein the operative constituent consists of the effective amount of menaquinone-7, the effective amount of ubiquinone, the effective amount of vitamin D, and an effective amount of the menaquinone-4.

7. The method of claim 1, wherein the operative constituent consists of the effective amount of menaquinone-7, the effective amount of ubiquinone, the effective amount of vitamin D, an effective amount of the cranberry extract, an effective amount of the *Astragalus*, and an effective amount of the *Ocimum tenuiflorum*.

8. The method of claim 1, further comprising: swishing the mouth slurry within the mouth of the user; and spitting the mouth slurry from the mouth of the user.

9. A method for using a toothpaste to promote a healthy oral microbiome, the method comprising:

provuding a toothbrush for a user, wherein the toothbrush comprises a handle and a set of bristles opposite the handle;

selecting a toothpaste that comprises a base constituent and an operative constituent;

placing a portion of the toothpaste on the set of bristles of the toothbrush;

brushing the teeth of a user;

producing a mouth slurry in the mouth of the user by the brushing;

swishing the mouth slurry within the mouth of the user; and spitting the mouth slurry from the mouth of the user, wherein the operative constituent consists of an effective amount of menaquinone-7, an effective amount of ubiquinone, and an effective amount of vitamin D, and wherein the base constituent consists of one or more selected from the group consisting of calcium carbonate, silica, glycerine, and water.

10. A method for using a toothpaste to promote a healthy oral microbiome, the method comprising:

providing a toothbrush for a user, wherein the toothbrush comprises a handle and a set of bristles opposite the handle;

selecting a toothpaste that comprises a base constituent and an operative constituent;

placing a portion of the toothpaste on the set of bristles of the toothbrush;

brushing the teeth of a user;

producing a mouth slurry in the mouth of the user by the brushing;

swishing the mouth slurry within the mouth of the user; and spitting the mouth slurry from the mouth of the user, wherein the operative constituent consists of an effective amount of menaquinone-7, an effective amount of ubiquinone, an effective amount of vitamin D, and an effective amount of an *Astragalus* adaptogenic herb, and wherein the base constituent consists of one or more selected from the group consisting of calcium carbonate, silica, glycerine, and water.

* * * * *